(12) United States Patent
Li et al.

(10) Patent No.: US 10,865,430 B2
(45) Date of Patent: Dec. 15, 2020

(54) DEVICE AND METHOD OF PRODUCING ULTRA-LOW SULFUR BIODIESEL

(71) Applicant: Tangshan Jinlihai Biodiesel Corporation Limited, Tangshan (CN)

(72) Inventors: Aijun Li, Tangshan (CN); Hong Wang, Tangshan (CN); Guangming Wen, Tangshan (CN); Weiqing Chen, Tangshan (CN); Hongpeng Li, Tangshan (CN); Liyan Feng, Tangshan (CN); Liguang Feng, Tangshan (CN)

( * ) Notice: Subject to any disclaimer, the term of this patent is extended or adjusted under 35 U.S.C. 154(b) by 46 days.

(21) Appl. No.: 15/992,159

(22) Filed: May 29, 2018

(65) Prior Publication Data

US 2019/0048369 A1    Feb. 14, 2019

Related U.S. Application Data

(63) Continuation of application No. PCT/CN2017/000700, filed on Nov. 24, 2017.

(30) Foreign Application Priority Data

Aug. 10, 2017    (CN) .......................... 2017 1 0682299

(51) Int. Cl.
    *C12P 7/64*    (2006.01)
    *C10L 1/02*    (2006.01)
    (Continued)

(52) U.S. Cl.
    CPC .............. *C12P 7/649* (2013.01); *B01D 3/002* (2013.01); *B01D 3/009* (2013.01); *B01D 3/04* (2013.01);
    (Continued)

(58) Field of Classification Search
    CPC .......... B01D 3/002; B01D 3/04; B01D 3/009; B01D 3/106; B01D 3/146; B01D 3/30;
    (Continued)

(56) References Cited

U.S. PATENT DOCUMENTS

| 7,905,930 B2 * | 3/2011 | Oyler ...................... C10G 3/00 |
| | | 44/308 |
| 2017/0066984 A1 * | 3/2017 | Doyle et al. ............ C10L 1/026 |

FOREIGN PATENT DOCUMENTS

| CN | 102649920 A | 8/2012 |
| CN | 103173292 A | 6/2013 |

(Continued)

OTHER PUBLICATIONS

International Search Report of PCT/CN2017/000700, dated Apr. 18, 2018.
EPO Search Report of 17868495.7, dated Jul. 12, 2019.

*Primary Examiner* — Gautam Prakash
(74) *Attorney, Agent, or Firm* — W&K IP

(57) ABSTRACT

Provided is a device for producing ultra-low sulfur biodiesel. The device for producing ultra-low sulfur biodiesel is a two-stage processing device, comprising a two-stage purification unit, a two-stage enzyme reaction unit, a two-stage distillation unit, and a decompression rectification unit. The present invention is green and environment-friendly, effectively and completely removing sulfur-containing impurities from the raw material, eliminating the attack of a sulfur-containing group in the synthesis process on fatty acids, and providing sufficient conditions for obtaining ultra-low sulfur content methyl esters in the product section.

12 Claims, 2 Drawing Sheets

(51) Int. Cl.
*C07C 67/54* (2006.01)
*C11C 3/00* (2006.01)
*B01D 3/00* (2006.01)
*C11C 3/02* (2006.01)
*C11B 13/00* (2006.01)
*B01D 3/04* (2006.01)
*B01D 3/10* (2006.01)
*B01D 3/14* (2006.01)
*B01D 3/30* (2006.01)
*C10L 1/18* (2006.01)
*C12N 9/20* (2006.01)

(52) U.S. Cl.
CPC ............ *B01D 3/106* (2013.01); *B01D 3/146* (2013.01); *B01D 3/30* (2013.01); *C07C 67/54* (2013.01); *C10L 1/026* (2013.01); *C10L 1/1802* (2013.01); *C11B 13/00* (2013.01); *C11C 3/00* (2013.01); *C11C 3/003* (2013.01); *C11C 3/02* (2013.01); *C12N 9/20* (2013.01); *C12Y 301/01* (2013.01); *C10L 2200/0476* (2013.01); *C10L 2270/026* (2013.01); *C10L 2290/54* (2013.01); *Y02E 50/10* (2013.01)

(58) Field of Classification Search
CPC ... C11C 3/00; C11C 3/02; C11C 3/003; C07C 67/54; C07C 69/52; C12Y 301/01; C11B 13/00; C12N 9/20; C10L 1/026; C10L 1/082; C10L 2290/54; C10L 2270/026; C10L 2200/0476; Y02E 50/13
See application file for complete search history.

(56) References Cited

FOREIGN PATENT DOCUMENTS

| | | |
|---|---|---|
| CN | 105694999 A | 6/2016 |
| CN | 106675789 A | 5/2017 |
| WO | 2010002236 A1 | 3/2017 |

* cited by examiner

DEVICE AND METHOD OF PRODUCING ULTRA-LOW SULFUR BIODIESEL

CROSS-REFERENCE TO RELATED APPLICATIONS

This application is a continuation of International Patent Application No. PCT/CN2017/000700 with a filing date of Nov. 24, 2017, designating the United States, now pending, and further claims priority to Chinese Patent Application No. 201710682299.7 with a filing date of Aug. 10, 2017. The content of the aforementioned applications, including any intervening amendments thereto, are incorporated herein by reference.

TECHNICAL FIELD

The present invention relates to the field of biodiesel preparation, and in particular, to an environment-friendly preparation device and method of ultra-low sulfur biodiesel.

BACKGROUND

Biodiesel is a mixed fatty acid methyl ester produced after being reacted with methanol under the action of a catalyst with waste animal and vegetable oil as raw material, and can be mixed with petrochemical diesel for engine combustion, having the effect of environmental protection and emission reduction. Specifically:

Biodiesel contains high levels of oxygen and is fully burned, reducing the emission of nitrogen oxides and carbon monoxides.

Biodiesel is non-toxic and harmless, reducing the emission of toxic gases.

Biodiesel has low sulfur content, reducing the emission of sulfur dioxide.

Biodiesel raw material comes from nature, reducing the net increase in global carbon dioxide.

In recent years, with the encouragement of the country and the attention to the atmosphere from people, biodiesel, which is a new energy that can replace petrochemical diesel, has developed rapidly. At the same time, with the progress of society and the improvement of production technology, the standard of petrochemical diesel has also rapidly increased and the products have been continuously upgraded. At present, the sulfur content index of petrochemical diesel in China is controlled below 10 PPM. From the data of sulfur content, the low sulfur content of biodiesel is no longer an advantage. How to reduce the sulfur content of biodiesel has become a problem in the industry.

The sulfur content of conventional biodiesel products is between 50 PPM and 20 PPM. To obtain products with 10 ppm or lower sulfur content, further processing is required. The common method is cleaning or adsorption of desulfurizers. These methods are often costly or inefficient, and will impact other indicators of biodiesel.

SUMMARY

In view of the technical defects mentioned in the background art, the present invention provides an environment-friendly device for producing ultra-low sulfur biodiesel in which the sulfur content of biodiesel products is controlled below 1 PPM, and further provides a method of producing ultra-low sulfur biodiesel using such device.

The technical solution adopted by the present invention to achieve the above technical purpose is: a device for producing ultra-low sulfur biodiesel, wherein the device for producing ultra-low sulfur biodiesel is a two-stage processing device, which comprises a two-stage purification unit, a two-stage enzyme reaction unit, and a two-stage distillation unit, and further comprises a decompression rectification unit according to the production process; wherein the purification unit comprises a raw material storage tank, a heater, a purification tower, a mixer, and a centrifuge that are connected in order through a pipeline;

a raw material pump is installed on the pipeline between the raw material storage tank and the heater; an external pipe communicated with the heat source is installed on the heater; a circulation pump is installed on the pipeline between the heater and the purification tower, the lower part of the purification tower is communicated with a wastewater tank, the upper part of the purification tower is communicated with the mixer, and an external pipe communicated with high-pressure methanol water is installed on the mixer; the mixer is communicated with the centrifuge, the bottom of the centrifuge is communicated with the wastewater tank, and the upper part of the centrifuge is communicated with a primary elution raw material storage tank;

the device structure and the arrangement of the two-stage purification unit are the same; the elution raw material storage tank of a primary purification unit is the initial raw material storage tank of a secondary purification unit;

the enzyme reaction unit comprises a methanol storage tank, and a immobilized enzyme reaction bed, a crude glycerol storage tank, a high-speed centrifuge, and a crude methyl ester storage tank connected together in order through a pipeline;

the elution raw material storage tank of the secondary purification unit is communicated with the immobilized enzyme reaction bed through a pipeline; the immobilized enzyme reaction bed is also communicated with the methanol storage tank through a pipeline; the immobilized enzyme reaction bed is communicated with the centrifuge, and the centrifuge is communicated with the crude glycerol storage tank and the crude methyl ester storage tank, respectively;

the two-stage enzyme reaction units share a single methanol storage tank, the methanol storage tank is connected with the two-stage immobilized enzyme reaction beds through a pipeline, respectively, and a control valve is provided on the pipeline through which the methanol storage tank is communicated with the two-stage immobilized enzyme reaction beds, respectively; other device structures and arrangements are the same; the crude methyl ester storage tank of a primary esterification reaction unit is an initial raw material storage tank of a secondary esterification reaction unit;

the distillation unit comprises a molecular distillation tower and a high-coagulation product storage tank;

the crude methyl ester storage tank of the secondary esterification reaction unit is communicated with a primary molecular distillation tower in a primary distillation unit through a pipeline, the primary molecular distillation tower is communicated with a primary high-coagulation product storage tank and a secondary molecular distillation unit in a secondary distillation unit, respectively, and the secondary molecular distillation tower is communicated with a secondary high-coagulation product storage tank and a decompression rectification unit, respectively;

the decompression rectification unit comprises a decompression rectification tower and a tower overhead condenser;

the decompression rectification tower is communicated with the secondary molecular distillation tower through a pipeline, and a decompression rectification tower bottom circulation pump is installed on this part of the pipeline; the bottom of the decompression rectification tower is communicated with a black horn storage tank and the top thereof is communicated with a biodiesel product storage tank through a pipeline, and a decompression rectification tower overhead circulation pump is installed on this part of the pipeline; the tower overhead condenser is communicated with the decompression rectification tower and the biodiesel product storage tank through a pipeline, respectively; and the lower part of the decompression rectification tower is also provided with an external pipe that is communicated with a heat source.

High-pressure methanol water communicated through an external pipe is used in the purification unit, wherein the concentration of methanol contained in the methanol water is 2%-10%.

In the enzyme reaction unit, the molar ratio of methanol to oil in the primary immobilized enzyme reaction bed is 0.7-1:1, and the internal reaction environment temperature is 50-60° C.

In the enzyme reaction unit, the molar ratio of methanol to oil in the secondary immobilized enzyme reaction bed is 0.4-0.6:1, and the internal reaction environment temperature is 40-55° C.

In the distillation unit, the degree of vacuum in the primary molecular distillation tower is 50-100 Pa, and the environment temperature is 120-130° C.

In the distillation unit, the degree of vacuum in the secondary molecular distillation tower is 50-100 Pa, and the environment temperature is 125-135° C.

The device for producing ultra-low sulfur biodiesel comprises an enzyme reaction bed body and a methanol distributor;

wherein the immobilized enzyme reaction bed is a large plate-type enzyme reaction bed, i.e., a rectangular box structure arranged horizontally, and a catalyst is filled in the enzyme reaction bed;

the methanol distributor comprises an input branch pipe, an input manifold, and a nozzle; a plurality of input branch pipes are uniformly distributed along its length direction inside the box structure, each of the input branch pipes is communicated with the input manifold, and the input manifold is communicated with the methanol storage tank;

a one-way peristaltic pump is installed on the input manifold;

each of the input branch pipes is installed with a control valve, respectively;

the first part of the box structure is provided with an oil inlet pipe, which is communicated with an elution raw material storage tank in the purification unit; and the tail part thereof is provided with an output pipe, which is communicated with a centrifugal pump.

The input manifold of the primary immobilized enzyme reaction bed is communicated with the input manifold of the secondary immobilized enzyme reaction bed.

A plurality of nozzles are uniformly distributed on the input branch pipe provided inside the immobilized enzyme reaction bed.

The oil inlet pipe of the secondary immobilized enzyme reaction bed is communicated with the crude methyl ester storage tank in the primary enzyme reaction unit.

A method of producing ultra-low sulfur biodiesel is performed according to the following steps:

a. storing, by the raw material storage tank, a variety of waste animal and vegetable fats, turning on a raw material pump, a primary heater, a tower bottom circulation pump, and heat source, raising the temperature of the raw oil in a primary purification tower to 100° C. to 110° C., separating water from impurities into a wastewater tank, producing raw oil from the tower overhead and passing through the mixer, cleaning the raw oil using high-pressure methanol water, pressure-feeding the mixed liquid to the centrifuge, separating water from impurities into a wastewater tank, centrifuging primary purified raw oil to the elution raw material storage tank, and waiting for the next process;

b. storing, by the raw material storage tank, in sufficient quantity, turning on an oil pump, a secondary heater, a tower bottom circulation pump and heat source, raising the temperature of the raw oil in a secondary purification tower to 70° C. to 80° C., separating water from impurities into a wastewater tank, producing raw oil from the tower overhead and passing through the mixer, cleaning the raw oil using high-pressure methanol water, pressure-feeding the mixed liquid to the centrifuge, separating water from impurities into a wastewater tank, centrifuging a secondary purified raw oil to the elution raw material storage tank until the next process;

c. filling a catalyst and a methanol distributor in a primary immobilized enzyme reaction bed;

prior to starting, confirming that the elution raw material storage tank is rich in the raw material and the methanol storage tank is rich in methanol, turning on the oil pump, turning on a one-way peristaltic pump and turning on control valves on the input branch pipe in sequence when the raw material enters the primary immobilized enzyme reaction bed, performing transesterification of the raw material in the reactor in sequence, the reacted material self-flowing to a high-speed centrifuge, under the action of high-speed centrifugation, centrifuging the transesterified glycerol and water to a crude glycerol storage tank for direct sale or further purification, and centrifuging the crude methyl ester and unreacted raw material to a primary crude methyl ester storage tank until the next step;

d. the secondary immobilized enzyme reaction bed being the same as the primary immobilized ester reaction bed;

prior to starting, confirming that the primary crude methyl ester storage tank is rich in the material and the methanol storage tank is rich in methanol, turning on the oil pump, turning on a one-way peristaltic pump and turning on control valves on the input branch pipe in sequence when the raw material enters the secondary immobilized enzyme reaction bed, performing transesterification of the unreacted raw material in the reactor in sequence, adjusting the residence time of the material in the secondary immobilized enzyme reaction bed, the reacted material self-flowing to a high-speed centrifuge, under the action of high-speed centrifugation, centrifuging the transesterified glycerol and water to a crude glycerol storage tank for direct sale or further purification, and centrifuging the crude methyl ester to a secondary crude methyl ester storage tank until the next step;

e. turning on a primary molecular distillation tower to confirm that after the secondary crude methyl ester storage tank is rich in crude methyl ester, starting the continuous feeding, separating light-component high-conglutination products into a high-conglutination product storage tank, directly selling or refining the products, and making heavy components enter the secondary molecular distillation tower;

f. turning on the secondary molecular distillation tower after the primary molecular distillation tower is fed, after the primary molecular distillation heavy components are produced, starting the continuous feeding, separating light-component high-conglutination products into a high-conglutination product storage tank, directly selling or refining the products, and making heavy components enter the decompression rectification tower;

g. turning on the decompression rectification tower bottom circulation pump, the heat source, the decompression rectification tower overhead circulation pump, the tower overhead condenser, and the cooling source 46 according to the route of the material, establishing the temperature gradient of the decompression rectification tower; after the level of the tower overhead is sufficient, turning on the valve slowly and maintaining the opening of the return valve, and producing the refined biodiesel product to the biodiesel product storage tank in which the product has a sulfur content less than 1 PPM for sale; and producing the vegetable asphalt which is liquid produced at the tower bottom to the black horn storage tank for sale.

In the method of producing ultra-low sulfur biodiesel, steps a and b are the raw material purification reaction completed by the two-stage purification unit;

steps c and d are the esterification reaction completed by the two-stage esterification reaction unit;

steps e and f are the distillation reaction completed by the two-stage distillation reaction unit; and step g is the decompression rectification reaction completed by the decompression rectification unit.

The present invention has the following characteristics:

1. This method produces only a small amount of easily-treated methanol wastewater, discharges no exhaust gas and waste residue, and is a green production technology.

2. This method washes using raw material glycol to effectively and completely removing sulfur-containing impurities from the raw material.

3. This method uses a two-step enzyme reaction bed, which provides a low-temperature and low-auxiliary material supply while maintaining a high conversion rate of feed oil, and under the mild catalytic action of organic enzymes, eliminates the attack of a sulfur-containing group in the synthesis process on fatty acids, and also makes glycerol and vegetable asphalt which are by-products be salt-free, and this is a clean production technology.

4. The product adopts two-stage molecular distillation prior to decompression distillation, which completely removes the short-chain molecules of a sulfur-containing group, and provides sufficient conditions for obtaining ultra-low sulfur content methyl esters in the product segment.

5. The decompression rectification tower is a packed tower. At the same time, a large-proportion return producing manner of the biodiesel tower overhead is used to ensure that the long-chain molecules of a sulfur-containing group are not entrained, providing sufficient conditions for obtaining ultra-low sulfur content methyl esters in the product segment.

6. This method has no manual operation and standing waiting process and has automatic production conditions.

Figure 1:
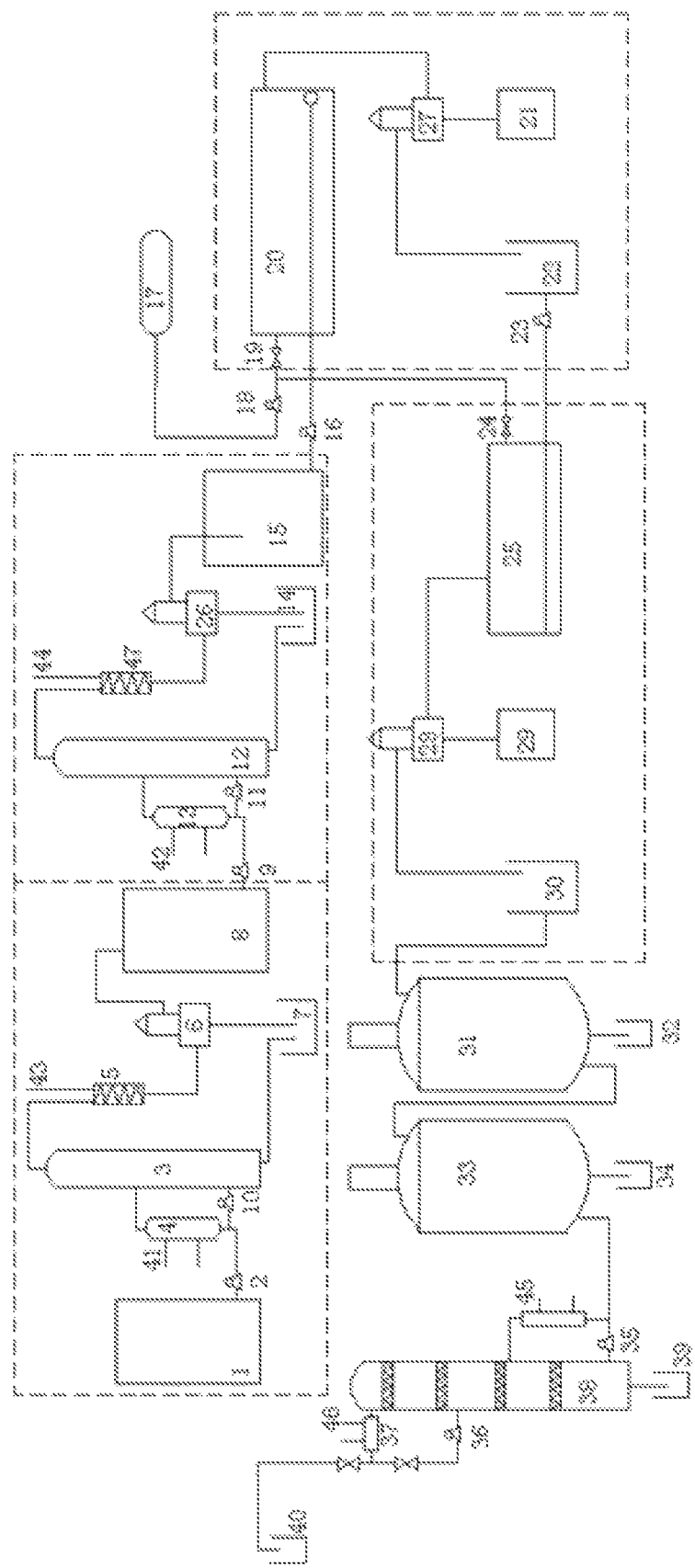
FIG. 1 is a schematic diagram illustrating a device according to the present invention.
Figure 2:
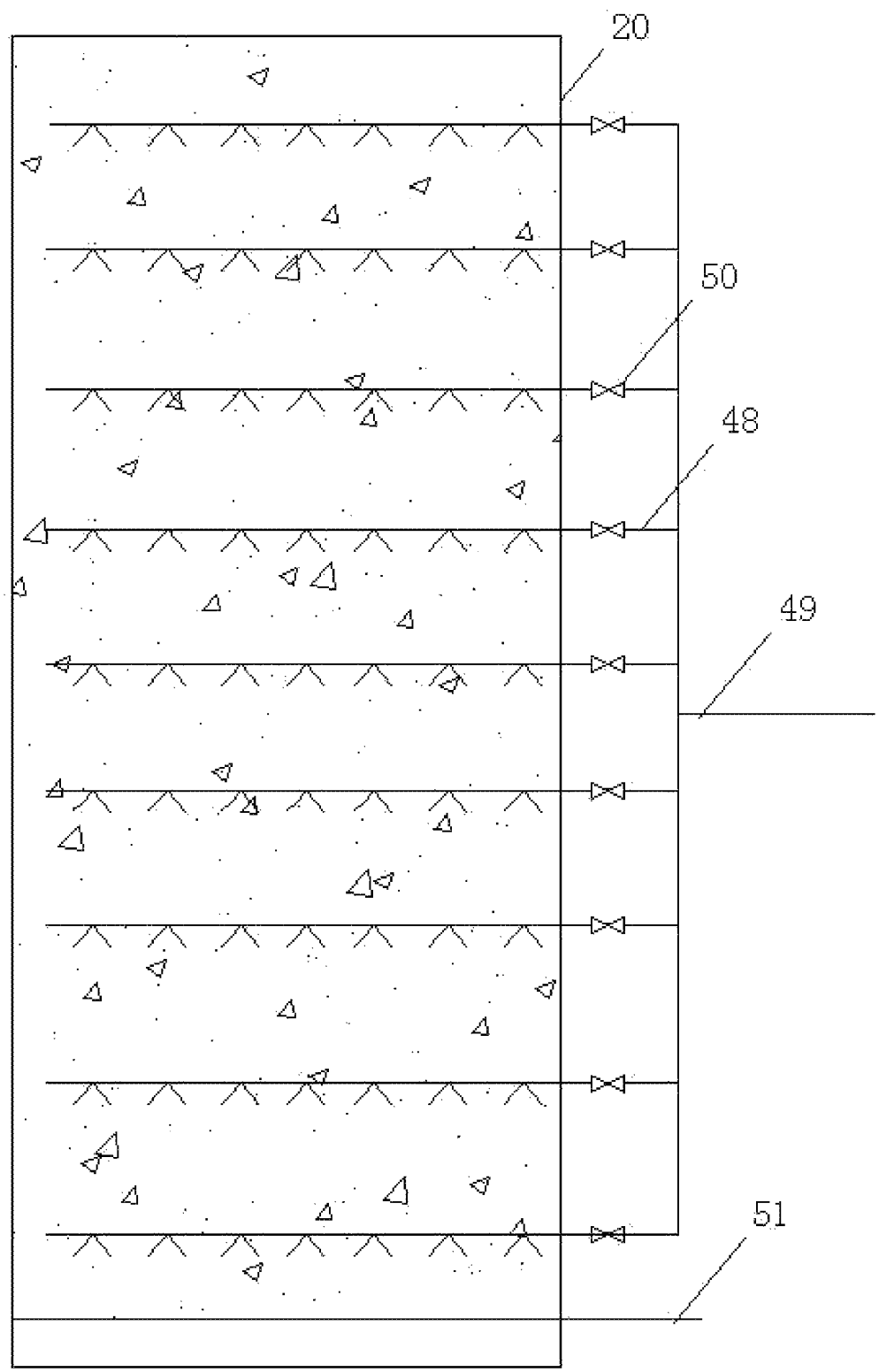
FIG. 2 is a schematic diagram illustrating the structure of an immobilized enzyme reaction bed according to the present invention.

In the drawings: a raw material storage tank 1, a raw material pump 2, a primary purification tower 3, a primary heater 4, a first pipeline mixer 5, a first high-speed centrifuge 6, a first wastewater tank 7, a primary elution raw material storage tank 8, a first oil pump 9, a first tower bottom circulation pump 10, a second tower bottom circulation pump 11, a secondary purification tower 12, a secondary heater 13, a second wastewater tank 14, a secondary elution raw material storage tank 15, a second oil pump 16, a methanol storage tank 17, a one-way peristaltic pump 18, a first control valve 19, a primary immobilized enzyme reaction bed 20, a primary crude glycerol storage tank 21, a primary crude methyl ester storage tank 22, a third oil pump 23, a second control valve 24, a secondary immobilized enzyme reaction bed 25, a second high-speed centrifuge 26, a third high-speed centrifuge 27, a fourth high-speed centrifuge 28, a secondary crude glycerol storage tank 29, a secondary coarse methyl ester storage tank 30, a primary molecular distillation tower 31, a first high-coagulation product storage tank 32, a secondary molecular distillation tower 33, a second high-coagulation product storage tank 34, a decompression rectification tower bottom circulation pump 35, a decompression rectification tower overhead circulation pump 36, a tower overhead condenser 37, a decompression rectification tower 38, a black horn tank 39, a biodiesel product storage tank 40, a first heat source external pipe 41, a second heat source external pipe 42, a first high-pressure methanol water external pipe 43, a second high-pressure methanol water external pipe 44, a third heat source external pipe 45, a cold source external pipe 46, and a second pipeline mixer 47.

In order to more clearly illustrate the technical solutions of the embodiments of the present invention, the accompanying drawings required in the embodiments will be briefly described below. It should be understood that the accompanying drawings below merely illustrate some embodiments of the present invention, and therefore should be regarded as a limitation on the scope. For those skilled in the art, other related drawings may also be obtained based on these accompanying drawings without any creative work.

DESCRIPTION OF EMBODIMENTS

The present invention will be described in detail below with reference to the accompanying drawings and embodiments.

To make the objectives, technical solutions, and advantages of the embodiments of the present invention clearer, the technical solutions in the embodiments of the present invention will be clearly described with reference to the accompanying drawings in the embodiments of the present invention. Obviously, the described embodiments form a part of the embodiments of the present invention, rather than all of the embodiments. The components of the embodiments of the present invention, which are generally described and illustrated in the figures herein, may be arranged and designed in a wide variety of different configurations.

It should be noted that similar reference numerals and letters refer to similar items in the following figures, and therefore, once an item is defined in one figure, the item needs not be further defined and explained in subsequent figures.

In the description of the present invention, it should be noted that the orientation or position relationship indicated by the terms such as "center", "upper", "lower", "left", "right", "vertical", "horizontal", "inner", "outer", etc. is based on the orientation or position relationship shown in the accompanying drawings, or the orientation or position relationship that is conventionally placed when the product of the present invention is used, and is merely for ease of description of the present invention and simplified description, rather than indicating or implying that the device or component referred to must have a particular orientation and must be constructed and operated in a particular orientation, and therefore should not be construed to limit the present invention. Furthermore, the terms such as "first," "second," "third," etc. are used merely to distinguish one description from another, and are not to be construed as indicating or implying relative importance.

In addition, the terms such as "horizontal," "vertical," "drape," etc. do not indicate a requirement that the parts are absolutely horizontal or overhanging, but may be slightly inclined. For example, "horizontal" merely means that its direction is more horizontal than "vertical," rather than meaning that the structure must be completely horizontal, but may be slightly inclined.

In the description of the present invention, it should also be noted that the terms such as "provide", "install", "link", and "connect" should be interpreted broadly unless specifically defined or limited otherwise. For example, the terms may indicate an immobilized connection or a detachable connection, or an integral connection; the terms may indicate a mechanical connection or an electrical connection; the terms may indicate a direct connection or an indirect connection through an intermediary medium or a communication inside two components. For a person of ordinary skill in the art, the specific meanings of the above terms in the present invention may be understood in specific situations.

The device for producing ultra-low sulfur biodiesel disclosed in the present invention is a two-stage processing device, which comprises a two-stage purification unit, a two-stage enzyme reaction unit, and a two-stage distillation unit, and further comprises a decompression rectification unit according to the production process, wherein the decompression rectification unit is a single-stage processing unit.

The purification unit comprises a raw material storage tank, a heater, a purification tower, a mixer, and a centrifuge that are connected in order through a pipeline.

In the first-stage purification unit: a raw material pump 2 is installed on the pipeline between the raw material storage tank 1 and a primary heater 4. A first heat source communicating external pipe 41 communicated with the external heat source is installed on the primary heater 4. A first tower bottom circulation pump 10 is installed on the pipeline between the primary heater 4 and the primary purification tower 3. The lower part of the primary purification tower 3 is communicated with a first wastewater tank 7, the upper part of the primary purification tower 3 is communicated with the first pipeline mixer 5, and a first high-pressure methanol water external pipe 43 communicated with methanol water is installed on the first pipeline mixer 5. The first pipeline mixer 5 is communicated with the first high-speed centrifuge 6, the bottom of the first high-speed centrifuge 6 is communicated with the first wastewater tank 7, and the upper part of the first high-speed centrifuge 6 is communicated with a primary elution raw material storage tank 8.

The device structure and the arrangement of the two-stage purification unit are the same.

In the second-stage purification unit: the primary elution raw material storage tank 8 is the initial raw material storage tank of a secondary purification unit. A first oil pump 9 is installed on the pipeline between the primary elution raw material storage tank 8 and a secondary heater 13. A second heat source communicating external pipe 42 communicated with the external heat source is installed on the secondary heater 13. A second tower bottom circulation pump 11 is installed on the pipeline between the secondary heater 13 and the secondary purification tower 12. The lower part of the secondary purification tower 12 is communicated with a second wastewater tank 14, the upper part of the secondary purification tower 12 is communicated with the second pipeline mixer 47, and a second high-pressure methanol water external pipe 44 communicated with methanol water is installed on the second pipeline mixer 47. The second pipeline mixer 47 is communicated with the second high-speed centrifuge 26, the bottom of the second high-speed centrifuge 26 is communicated with the second wastewater tank 14, and the upper part of the second high-speed centrifuge 26 is communicated with a second elution raw material storage tank 15.

The external heat source can be the same or a different heat source supply. The methanol water supply source may be the same or a different supply source.

The enzyme reaction unit comprises a methanol storage tank, and a immobilized enzyme reaction bed, a crude glycerol storage tank, a high-speed centrifuge, and a crude methyl ester storage tank connected together in order through a pipeline.

In the primary enzyme reaction unit: the secondary elution raw material storage tank 15 is communicated with the primary immobilized enzyme reaction bed 20 through a pipeline, and a second oil pump 16 is installed on this part of the pipeline. The primary immobilized enzyme reaction bed 20 is also communicated with the methanol storage tank 17 through a pipeline, and a single peristaltic pump 18 and a first control valve 19 are installed on this part of the pipeline; the primary immobilized enzyme reaction bed 20 is communicated with a third high-speed centrifuge 27, and the third high-speed centrifuge 27 is communicated with the primary crude glycerol storage tank 21 and the primary crude methyl ester storage tank 22, respectively.

In the second-stage enzyme reaction unit: other device structures and arrangements are the same; the primary crude methyl ester storage tank 22 of a primary esterification reaction unit is an initial raw material storage tank of a secondary esterification reaction unit. The primary crude methyl ester storage tank 22 is communicated with the secondary immobilized enzyme reaction bed 25, and a third oil pump 23 is installed on this part of the pipeline. The secondary immobilized enzyme reaction bed 25 is also communicated with the methanol storage tank 17 through a pipeline, and a second control valve 24 is provided on this part of the pipeline which shares a single peristaltic pump 18 with the pipeline on the primary enzyme reaction bed. The secondary immobilized enzyme reaction bed 25 is communicated with the fourth high-speed centrifuge 28, and the fourth high-speed centrifuge 28 is communicated with the secondary crude glycerol storage tank 29 and the secondary crude methyl ester storage tank 30, respectively.

The two-stage enzyme reaction units share a single methanol storage tank 17, the methanol storage tank is connected with the two-stage immobilized enzyme reaction beds through a pipeline, respectively, and a control valve is provided on the pipeline through which the methanol storage tank is communicated with the two-stage immobilized enzyme reaction beds, respectively.

The distillation unit comprises a molecular distillation tower and a high-coagulation product storage tank.

The secondary crude methyl ester storage tank 30 is communicated with a primary molecular distillation tower 31 through a pipeline, the primary molecular distillation tower is communicated with a primary high-coagulation product storage tank 32 and a secondary molecular distillation unit 33 in a secondary distillation unit, respectively, and the secondary molecular distillation tower 33 is communicated with a secondary high-coagulation product storage tank 34 and a decompression rectification unit, respectively.

A distillation reaction is performed on the material resulting from the secondary esterification reaction through two molecular distillation towers.

The decompression rectification unit comprises a decompression rectification tower and a tower overhead condenser.

The decompression rectification tower 38 is communicated with the secondary molecular distillation tower 33 through a pipeline, and a decompression rectification tower bottom circulation pump 35 is installed on this part of the pipeline. The bottom of the decompression rectification tower 38 is communicated with a black horn storage tank 39 and the top thereof is communicated with a biodiesel product storage tank 40 through a pipeline, and a decompression rectification tower overhead circulation pump 36 is installed on this part of the pipeline. The tower overhead condenser 37 is communicated with the decompression rectification tower 38 and the biodiesel product storage tank 40 through a pipeline, respectively. The lower part of the decompression rectification tower 38 is also provided with a third heat source external pipe 45 that is communicated with an external heat source.

A return valve and a production valve are also provided on the pipeline between the decompression distillation tower 38 and the biodiesel product storage tank 40 to control the production and return of the oil product.

Preferably, the tower overhead condenser 37 is also communicated with an external cold source through a cold source external pipe 46.

The enzyme reaction device comprises an enzyme reaction bed body and a methanol distributor. The immobilized enzyme reaction bed is a large plate-type enzyme reaction bed, i.e., a rectangular box structure arranged horizontally, and a catalyst is filled in the enzyme reaction bed. Preferably, the immobilized lipase is used as the catalyst.

The methanol distributor comprises an input branch pipe 48, an input manifold 49, and a nozzle 50. A plurality of input branch pipes 48 are uniformly distributed along its length direction inside the enzyme reaction bed, each of the input branch pipes is communicated with the input manifold 49, and the input manifold is communicated with the methanol storage tank 17. Each of the input branch pipes is installed with a control valve, respectively. The plurality of control valves are combined to form a first control valve 19 or a second control valve 24, and the first control valve 19 or the second control valve 24 is a combination of valves, respectively.

A one-way peristaltic pump is installed on the input manifold. The branches on the input manifold are communicated with the input branches of the two-stage enzyme reaction bed, sharing a single peristaltic pump.

The first part of the box structure is provided with an oil inlet pipe, which is communicated with an elution raw material storage tank in the purification unit; and the tail part thereof is provided with an output pipe, which is communicated with a centrifugal pump. The input manifold of the primary immobilized enzyme reaction bed is communicated with the input manifold of the secondary immobilized enzyme reaction bed.

A plurality of nozzles are uniformly distributed on the input branch pipe provided inside the immobilized enzyme reaction bed. Most preferably, the input branch pipe is provided in the longitudinally central position of the esterification reaction bed and is provided inside the catalyst.

The method of producing ultra-low sulfur biodiesel using the device is performed according to the following steps.

a. The raw material storage tank 1 stores a variety of waste animal and vegetable fats, turning on a raw material pump 2, a primary heater 4, a first tower bottom circulation pump 10, and a first heat source external pipe 41, raising the temperature of the raw oil in a primary purification tower 3 to 100° C. to 110° C., separating water from impurities into a first wastewater tank 7, producing raw oil from the tower overhead and passing through the first pipeline mixer 5, cleaning the raw oil using high-pressure methanol water introduced by the first high-pressure methanol water external pipe 43 in which the methanol water contains methanol at a concentration of 2% to 10% and the water temperature is 70° C., pressure-feeding the mixed liquid to the first high-speed centrifuge 6, separating water from impurities into the first wastewater tank 7, centrifuging primary purified raw oil to the primary elution raw material storage tank 8, and waiting for the next process.

b. The primary elution raw material storage tank 8 stores in sufficient quantity, turning on a first oil pump 9, a secondary heater 13, a second tower bottom circulation pump 11 and a second heat source external pipe 42, raising the temperature of the raw oil in a secondary purification tower 12 to 70° C. to 80° C., separating water from impurities into a second wastewater tank 14, producing raw oil from the tower overhead and passing through the second pipeline mixer 47, cleaning the raw oil using high-pressure methanol water introduced by the second high-pressure methanol water external pipe 44 in which the methanol water contains methanol at a concentration of 2% to 10%, pressure-feeding the mixed liquid to the second high-speed centrifuge 26, separating water from impurities into a second wastewater tank 14, and centrifuging a secondary purified raw oil to the secondary elution raw material storage tank 15 until the next process.

c. The primary immobilized enzyme reaction bed 20 is a large plate-type enzyme reaction bed which is filled with an immobilized lipase and a methanol distributor. The methanol distributor is uniformly distributed in the entire reaction bed channel. The distributor has both a regulating valve of a master controller and a regulating valve of each branch. Prior to starting, it is confirmed that the secondary elution raw material storage tank 15 is rich in the raw material and the methanol storage tank 17 is rich in methanol, turning on the second oil pump 16, turning on a one-way peristaltic pump 18 and turning on each of control valves in the first control valve 19 in sequence when the raw material enters the primary immobilized enzyme reaction bed 20 in which the total molar ratio of methanol to oil is 0.7-1:1 and the temperature is 50-60° C., performing transesterification of the raw material in the reactor in sequence, adjusting the residence time of the material in the primary immobilized enzyme reaction bed 20 so that the conversion rate of the material is more than 80%, the reacted material self-flowing to a third high-speed centrifuge 27, under the action of high-speed centrifugation, centrifuging the transesterified glycerol and water to a primary crude glycerol storage tank 21 for direct sale or further purification, and centrifuging the crude methyl ester and unreacted raw material to a primary crude methyl ester storage tank 22 until the next step.

d. The secondary immobilized enzyme reaction bed 25 is a large plate-type enzyme reaction bed which is filled with an immobilized lipase and a methanol distributor. The methanol distributor is uniformly distributed in the entire reaction bed channel. The distributor has both a regulating valve of a master controller and a regulating valve of each branch. Prior to starting, it is confirmed that the primary crude methyl ester storage tank 22 is rich in the material and the methanol storage tank 17 is rich in methanol, turning on the third oil pump 23, turning on a one-way peristaltic pump 18 and turning on each of branch control valves in the second control valve 24 in sequence when the raw material enters the secondary immobilized enzyme reaction bed 25 in which the total molar ratio of methanol to oil is 0.4:1 to 0.6:1 and the temperature is 40-55° C., performing transesterification of the unreacted raw material in the reactor in sequence, adjusting the residence time of the material in the secondary immobilized enzyme reaction bed 25 so that the total conversion rate of the material is more than 98%, the reacted material self-flowing to a fourth high-speed centrifuge 28, under the action of high-speed centrifugation, centrifuging the transesterified glycerol and water to a secondary crude glycerol storage tank 29 for direct sale or further purification, and centrifuging the crude methyl ester to a secondary crude methyl ester storage tank 30 until the next step.

e. A primary molecular distillation tower 31 is turned on with the degree of vacuum of 50 to 100 Pa and the temperature of 120 to 130° C. It is confirmed that after the secondary crude methyl ester storage tank 30 is rich in crude methyl ester, the continuous feeding is started, separating light-component high-conglutination products into a high-conglutination product storage tank 32, directly selling or refining the products, and making heavy components enter the secondary molecular distillation tower 33.

f. The secondary molecular distillation tower 33 is turned on after the primary molecular distillation tower 31 is fed with the degree of vacuum of 50 to 100 Pa and the temperature of 125 to 135° C. After the primary molecular distillation heavy components are produced, the continuous feeding is started, separating light-component high-conglutination products into a high-conglutination product storage tank 34, directly selling or refining the products, and making heavy components enter the decompression rectification tower 38.

g. The decompression rectification tower bottom circulation pump 35, the third heat source external pipe 45, the decompression rectification tower overhead circulation pump 36, the tower overhead condenser 37, and the cooling source 46 are turned on according to the route of the material, establishing the temperature gradient of the decompression rectification tower 38, after the level of the tower overhead is sufficient, turning on the valve slowly and maintaining the opening of the return valve, producing the refined biodiesel product to the biodiesel product storage tank 40 in which the product has a sulfur content less than 1 PPM for sale, and producing the vegetable bitumen which is liquid produced at the tower bottom to the black horn storage tank 39 for sale.

The present invention is further described below based on actual embodiments. The device name in the embodiment is an abbreviation, and the name label is used as the reference.

Embodiment 1

Acidified Oil (Acid Number 160 mgKOH/g)

The raw material storage tank 1 has 20 tons of acidified oil. The raw material pump 2, the primary heater 4, the bottom circulation pump 10 and the heat source 41 are turned on, raising the temperature of the raw oil in a primary purification tower 3 to 100° C., separating water from impurities into a wastewater tank 7, producing raw oil from the tower overhead and passing through the pipeline mixer 5, cleaning the raw oil using high-pressure methanol water 43 in which the methanol water contains methanol at a concentration of 3% and the water temperature is 70° C., pressure-feeding the mixed liquid to the high-speed centrifuge 6, separating water from impurities into the wastewater tank 7, and centrifuging primary purified raw oil to the elution raw material storage tank 8 at a total of 19.1 tons. The oil pump 9 is turned on to perform secondary purification. The methanol water contains methanol at a concentration of 3% and primary purified raw oil is centrifuged to the elution raw material storage tank 15 at a total of 19 tons. It is confirmed that the methanol storage tank 17 is rich in methanol, turning on the oil pump 16, turning on a one-way peristaltic pump 18 and turning on the control valve 19 in sequence when the raw material enters the primary immobilized enzyme reaction bed 20 in which the total molar ratio of methanol to oil is 0.7:1 and the temperature is 50° C., performing transesterification of the raw material in the reactor in sequence in which the residence time of the material in the primary immobilized enzyme reaction bed 20 is 20 hours so that the conversion rate of the material is 85%, the reacted material self-flowing to a high-speed centrifuge 27, under the action of high-speed centrifugation, centrifuging the transesterified glycerol and water to a primary crude glycerol storage tank 21 for further purification to 80% for sale, and centrifuging the crude methyl ester and unreacted raw material to a primary crude methyl ester storage tank 22 at a total of 19.05 tons.

The oil pump 23 is turned on, turning on the control valve 24 in sequence when the raw material enters the secondary immobilized enzyme reaction bed 25 in which the total molar ratio of methanol to oil is 0.5:1 and the temperature is 50° C., performing transesterification of the unreacted raw material in the reactor in sequence in which the residence time of the material in the secondary immobilized enzyme reaction bed 25 is 18 hours so that the total conversion rate of the material is 98.5%, the reacted material self-flowing to a high-speed centrifuge 28, under the action of high-speed centrifugation, centrifuging the transesterified glycerol and water to a crude glycerol storage tank 29 for further purification to 80% for sale, and centrifuging the crude methyl ester to a secondary crude methyl ester storage tank 30 at a total of 19.06 tons. The primary molecular distillation tower 31 is turned on with the degree of vacuum of 50 Pa and the temperature of 120° C. The secondary molecular distillation tower 33 is turned on after the primary molecular distillation tower 31 is fed with the degree of vacuum of 50 Pa and the temperature of 125° C. Light-component high-conglutination products are separated, and heavy components enter the decompression rectification tower 38. After the level of the tower overhead is sufficient, the valve is turned on slowly, and the refined biodiesel product is produced to the biodiesel product storage tank 40 in which the product has a sulfur content less than 1 PPM at a total of 17 tons.

The test indicators are shown in Table 1.

Embodiment 2

Catering Waste Oil (Acid Number 20 mgKOH/g)

The raw material storage tank 1 has 20 tons of acidified oil. The raw material pump 2, the primary heater 4, the bottom circulation pump 10 and the heat source 41 are turned on, raising the temperature of the raw oil in a primary purification tower 3 to 105° C., separating water from impurities into a wastewater tank 7, producing raw oil from the tower overhead and passing through the pipeline mixer 5, cleaning the raw oil using high-pressure methanol water 43 in which the methanol water contains methanol at a concentration of 5% and the water temperature is 70° C., pressure-feeding the mixed liquid to the high-speed centrifuge 6, separating water from impurities into the wastewater tank 7, and centrifuging primary purified raw oil to the elution raw material storage tank 8 at a total of 19.5 tons. The oil pump 9 is turned on to perform secondary purification. The methanol water contains methanol at a concentration of 5% and primary purified raw oil is centrifuged to the elution raw material storage tank 15 at a total of 19.4 tons. It is confirmed that the methanol storage tank 17 is rich in methanol, turning on the oil pump 16, turning on a one-way peristaltic pump 18 and turning on the control valve 19 in sequence when the raw material enters the primary immobilized enzyme reaction bed 20 in which the total molar ratio of methanol to oil is 0.7:1 and the temperature is 50° C., performing transesterification of the raw material in the reactor in sequence in which the residence time of the material in the primary immobilized enzyme reaction bed 20 is 25 hours so that the conversion rate of the material is 85%, the reacted material self-flowing to a high-speed centrifuge 27, under the action of high-speed centrifugation, centrifuging the transesterified glycerol and water to a primary crude glycerol storage tank 21 for sale, and centrifuging the crude methyl ester and unreacted raw material to a primary crude methyl ester storage tank 22 at a total of 19.3 tons.

The oil pump 23 is turned on, turning on the control valve 24 in sequence when the raw material enters the secondary immobilized enzyme reaction bed 25 in which the total molar ratio of methanol to oil is 0.5:1 and the temperature is 55° C., performing transesterification of the unreacted raw material in the reactor in sequence in which the residence time of the material in the secondary immobilized enzyme reaction bed 25 is 15 hours so that the total conversion rate of the material is 99%, the reacted material self-flowing to a high-speed centrifuge 28, under the action of high-speed centrifugation, centrifuging the transesterified glycerol and water to a crude glycerol storage tank 29 for sale, and centrifuging the crude methyl ester to a secondary crude methyl ester storage tank 30 at a total of 19.3 tons. The primary molecular distillation tower 31 is turned on with the degree of vacuum of 50 Pa and the temperature of 120° C. The secondary molecular distillation tower 33 is turned on after the primary molecular distillation tower 31 is fed with the degree of vacuum of 50 Pa and the temperature of 125° C. Light-component high-conglutination products are separated, and heavy components enter the decompression rectification tower 38. After the level of the tower overhead is sufficient, the valve is turned on slowly, and the refined biodiesel product is produced to the biodiesel product storage tank 40 in which the product has a sulfur content less than 1 PPM at a total of 18 tons.

The test indicators are shown in Table 1.

TABLE 1

Example detection indicators

| Test Item | Example 1 | Example 2 |
|---|---|---|
| Sulfur content (ISO20846) | 0.3 mg/kg | 0.4 mg/kg |
| % of raw material yield | 85% | 90% |

We claim:

1. A device for producing ultra-low sulfur biodiesel, wherein the device for producing ultra-low sulfur biodiesel is a two-stage processing device, which comprises a two-stage purification unit, a two-stage enzyme reaction unit, and a two-stage distillation unit, and further comprises a decompression rectification unit according to the production process; and wherein the purification unit comprises a raw material storage tank, a heater, a purification tower, a mixer, and a centrifuge that are connected in order through a pipeline;

a raw material pump is installed on the pipeline between the raw material storage tank and the heater; an external pipe communicated with the heat source is installed on the heater; a circulation pump is installed on the pipeline between the heater and the purification tower; the lower part of the purification tower is communicated with a wastewater tank, the upper part of the purification tower is communicated with the mixer, and an external pipe communicated with high-pressure methanol water is installed on the mixer; the mixer is communicated with the centrifuge, the bottom of the centrifuge is communicated with the wastewater tank, and the upper part of the centrifuge is communicated with a primary elution raw material storage tank;

the device structure and the arrangement of the two-stage purification unit are the same; the elution raw material storage tank of a primary purification unit is the initial raw material storage tank of a secondary purification unit;

the enzyme reaction unit comprises a methanol storage tank, and a immobilized enzyme reaction bed, a crude glycerol storage tank, a high-speed centrifuge, and a crude methyl ester storage tank connected together in order through a pipeline;

the elution raw material storage tank of the secondary purification unit is communicated with the immobilized enzyme reaction bed through a pipeline; the immobilized enzyme reaction bed is also communicated with the methanol storage tank through a pipeline; the immobilized enzyme reaction bed is communicated with the centrifuge, and the centrifuge is communicated with the crude glycerol storage tank and the crude methyl ester storage tank, respectively;

the two-stage enzyme reaction units share a single methanol storage tank, the methanol storage tank is connected with each of the two-stage immobilized enzyme reaction beds through a pipeline, and a control valve is provided on the pipeline through which the methanol storage tank is communicated with each of the two-stage immobilized enzyme reaction beds; the crude methyl ester storage tank of a primary esterification reaction unit is an initial raw material storage tank of a secondary esterification reaction unit;

the distillation unit comprises a molecular distillation tower and a high-coagulation product storage tank;

the crude methyl ester storage tank of the secondary esterification reaction unit is communicated with a primary molecular distillation tower in a primary distillation unit through a pipeline, the primary molecular distillation tower is communicated with a primary high-coagulation product storage tank and a secondary molecular distillation unit in a secondary distillation unit, respectively, and the secondary molecular distillation tower is communicated with a secondary high-coagulation product storage tank and a decompression rectification unit, respectively;

the decompression rectification unit comprises a decompression rectification tower and a tower overhead condenser;

the decompression rectification tower is communicated with the secondary molecular distillation tower through a pipeline, and a decompression rectification tower bottom circulation pump is installed on this part of the pipeline; the bottom of the decompression rectification tower is communicated with a residue storage tank and the top thereof is communicated with a biodiesel product storage tank through a pipeline, and a decompression rectification tower overhead circulation pump is installed on this part of the pipeline; the tower overhead condenser is communicated with the decompression rectification tower and the biodiesel product storage tank through a pipeline, respectively; and the lower part of the decompression rectification tower is also provided with an external pipe that is communicated with a heat source.

2. The device for producing ultra-low sulfur biodiesel according to claim 1, wherein high-pressure methanol water communicated through an external pipe is used in the purification unit, wherein the concentration of methanol contained in the methanol water is 2%-10%.

3. The device for producing ultra-low sulfur biodiesel according to claim 1, wherein in the enzyme reaction unit, the molar ratio of methanol to oil in the primary immobilized enzyme reaction bed is 0.7-1:1, and the internal reaction environment temperature is 50-60° C.

4. The device for producing ultra-low sulfur biodiesel according to claim 1, wherein in the enzyme reaction unit, the molar ratio of methanol to oil in the secondary immobilized enzyme reaction bed is 0.4-0.6:1, and the internal reaction environment temperature is 40-55° C.

5. The device for producing ultra-low sulfur biodiesel according to claim 1, wherein in the distillation unit, the degree of vacuum in the primary molecular distillation tower is 50-100 Pa, and the environment temperature is 120-130° C.

6. The device for producing ultra-low sulfur biodiesel according to claim 1, wherein in the distillation unit, the degree of vacuum in the secondary molecular distillation tower is 50-100 Pa, and the environment temperature is 125-135° C.

7. The device for producing ultra-low sulfur biodiesel according to claim 1, comprising: an enzyme reaction bed body and a methanol distributor;
wherein the immobilized enzyme reaction bed is a large plate-shaped enzyme reaction bed, and a catalyst is filled in the enzyme reaction bed;
the methanol distributor comprises an input branch pipe, an input manifold, and a nozzle; a plurality of input branch pipes are uniformly distributed along its length direction inside the box structure, each of the input branch pipes is communicated with the input manifold, and the input manifold is communicated with the methanol storage tank;
a one-way peristaltic pump is installed on the input manifold;
each of the input branch pipes is installed with a control valve, respectively;
the first part of the box structure is provided with an oil inlet pipe, which is communicated with an elution raw material storage tank in the purification unit; and the tail part thereof is provided with an output pipe, which is communicated with a centrifugal pump.

8. The device for producing ultra-low sulfur biodiesel according to claim 7, wherein the input manifold of the primary immobilized enzyme reaction bed is communicated with the input manifold of the secondary immobilized enzyme reaction bed.

9. The device for producing ultra-low sulfur biodiesel according to claim 7, wherein a plurality of nozzles are uniformly distributed on the input branch pipe provided inside the immobilized enzyme reaction bed.

10. The device for producing ultra-low sulfur biodiesel according to claim 7, wherein the oil inlet pipe of the secondary immobilized enzyme reaction bed is communicated with the crude methyl ester storage tank in the primary enzyme reaction unit.

11. A method of producing ultra-low sulfur biodiesel using the device according to claim 1, which is performed according to the following steps:
   a. storing, by the raw material storage tank, a variety of waste animal and vegetable fats, turning on a raw material pump, a primary heater, a tower bottom circulation pump, and heat source, raising the temperature of the raw oil in a primary purification tower to 100° C. to 110° C., separating water from impurities into a wastewater tank, producing raw oil from the tower overhead and passing through the mixer, cleaning the raw oil using high-pressure methanol water, pressure-feeding the mixed liquid to the centrifuge, separating water from impurities into a wastewater tank, centrifuging primary purified raw oil to the elution raw material storage tank, and waiting for the next process;
   b. storing, by the raw material storage tank, in sufficient quantity, turning on an oil pump, a secondary heater, a tower bottom circulation pump and heat source, raising the temperature of the raw oil in a secondary purification tower to 70° C. to 80° C., separating water from impurities into a wastewater tank, producing raw oil from the tower overhead and passing through the mixer, cleaning the raw oil using high-pressure methanol water, pressure-feeding the mixed liquid to the centrifuge, separating water from impurities into a wastewater tank, centrifuging a secondary purified raw oil to the elution raw material storage tank until the next process;
   c. filling a catalyst and a methanol distributor in a primary immobilized enzyme reaction bed;
   prior to starting, confirming that the elution raw material storage tank is rich in the raw material and the methanol storage tank is rich in methanol, turning on the oil pump, turning on a one-way peristaltic pump and turning on control valves on the input branch pipe in sequence when the raw material enters the primary immobilized enzyme reaction bed, performing transesterification of the raw material in the reactor in sequence, the reacted material self-flowing to a high-speed centrifuge, under the action of high-speed centrifugation, centrifuging the transesterified glycerol and water to a crude glycerol storage tank for direct sale or further purification, and centrifuging the crude methyl ester and unreacted raw material to a primary crude methyl ester storage tank until the next step;
   d. the secondary immobilized enzyme reaction bed being the same as the primary immobilized ester reaction bed;
   prior to starting, confirming that the primary crude methyl ester storage tank is rich in the material and the methanol storage tank is rich in methanol, turning on the oil pump, turning on a one-way peristaltic pump and turning on control valves on the input branch pipe in sequence when the raw material enters the secondary immobilized enzyme reaction bed, performing transesterification of the unreacted raw material in the reactor in sequence, adjusting the residence time of the material in the secondary immobilized enzyme reaction bed, the reacted material self-flowing to a high-speed centrifuge, under the action of high-speed centrifugation, centrifuging the transesterified glycerol and water to a crude glycerol storage tank for direct sale or further purification, and centrifuging the crude methyl ester to a secondary crude methyl ester storage tank until the next step;

e. turning on a primary molecular distillation tower to confirm that after the secondary crude methyl ester storage tank is rich in crude methyl ester, starting the continuous feeding, separating light-component high-conglutination products into a high-conglutination product storage tank, directly selling or refining the products, and making heavy components enter the secondary molecular distillation tower;

f. turning on the secondary molecular distillation tower after the primary molecular distillation tower is fed, after the primary molecular distillation heavy components are produced, starting the continuous feeding, separating light-component high-conglutination products into a high-conglutination product storage tank, directly selling or refining the products, and making heavy components enter the decompression rectification tower;

g. turning on the decompression rectification tower bottom circulation pump, the heat source, the decompression rectification tower overhead circulation pump, the tower overhead condenser, and the cooling source 46 according to the route of the material, establishing the temperature gradient of the decompression rectification tower; after the level of the tower overhead is sufficient, turning on the valve slowly and maintaining the opening of the return valve, and producing the refined biodiesel product to the biodiesel product storage tank in which the product has a sulfur content less than 1 PPM for sale; and producing the vegetable asphalt which is liquid produced at the tower bottom to the residue storage tank for sale.

12. The method of producing ultra-low sulfur biodiesel according to claim 11, wherein steps a and b are the raw material purification reaction completed by the two-stage purification unit;

steps c and d are the esterification reaction completed by the two-stage esterification reaction unit;

steps e and f are the distillation reaction completed by the two-stage distillation reaction unit; and step g is the decompression rectification reaction completed by the decompression rectification unit.

* * * * *